(12) United States Patent
Naito et al.

(10) Patent No.: US 8,034,924 B2
(45) Date of Patent: Oct. 11, 2011

(54) PROCESS FOR PRODUCTION OF CRYSTAL OF PURINE NUCLEOSIDE COMPOUND

(75) Inventors: Masaki Naito, Kawasaki (JP); Yoshitomo Kimura, Kawasaki (JP); Hiroya Ueda, Kawasaki (JP); Minoru Harada, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 287 days.

(21) Appl. No.: 12/504,839

(22) Filed: Jul. 17, 2009

(65) Prior Publication Data

US 2009/0326213 A1    Dec. 31, 2009

Related U.S. Application Data

(63) Continuation of application No. PCT/JP2007/074971, filed on Dec. 26, 2007.

(30) Foreign Application Priority Data

Jan. 19, 2007    (JP) .................................. 2007-010494

(51) Int. Cl.
*C07H 21/00*    (2006.01)

(52) U.S. Cl. ................... 536/25.4; 536/25.3; 536/25.41; 536/27.12; 536/27.1; 536/27.13; 536/27.2

(58) Field of Classification Search ........................ None
See application file for complete search history.

(56) References Cited

U.S. PATENT DOCUMENTS 5,451,671 A * 9/1995 Shiragami et al. ......... 536/27.12

OTHER PUBLICATIONS

Tai-Shun Lin, et al., "Synthesis and Antiviral Activity of Various 3'-Azido, 3'-Amino, 2',3'-Unsaturated, and 2',3'-Dideoxy Analogues of Pyrimidine Deoxyribonucleosides against Retroviruses[1]" Journal of Medicinal Chemistry, vol. 30, No. 2, 1987, pp. 440-444.

* cited by examiner

*Primary Examiner* — Patrick Lewis
(74) *Attorney, Agent, or Firm* — Oblon, Spivak, McClelland, Maier & Neustadt, L.L.P.

(57) ABSTRACT

Crystals of a purine nucleoside compound, particularly crystals of 2',3'-dideoxyinosine, which have excellent storage stability and have a concentration of phosphate attached to the crystal of 25 ppm or more, may be produce by: (1) preparing an aqueous solution containing phosphate ion ($PO_4^{3-}$) and a purine nucleoside compound; and (2) crystallizing the purine nucleoside compound from the aqueous solution.

20 Claims, No Drawings

PROCESS FOR PRODUCTION OF CRYSTAL OF PURINE NUCLEOSIDE COMPOUND

CROSS REFERENCES TO RELATED APPLICATIONS

This application is a continuation of International Patent Application No. PCT/JP2007/074971, filed on Dec. 26, 2007, and claims priority to Japanese Patent Application No. 2007-010494, filed on Jan. 19, 2007, both of which are incorporated herein by reference in their entireties.

BACKGROUND OF THE INVENTION

1. Field of the Invention

The present invention relates to methods for producing crystals of a purine nucleoside compound which have excellent storage stability, and particularly it relates to methods for producing crystals of 2',3'-dideoxyinosine (DDI) which are useful as a medical drug such as an anti-AIDS drug.

2. Discussion of the Background

A 2',3'-dideoxypurine nucleoside compound has an antiviral action which is usable for an anti-AIDS drug, for example. Therefore, it can be used as a medical drug (see, for example, JP-A 61-280500 and *J. Med. Chem.*, vol. 30, p. 440 (1987)). Various methods for producing a 2',3'-dideoxypurine nucleoside compound have been reported until now (see, for example, JP-A 01-224390, JP-A 02-117689, JP-A 02-291291, JP-A 03-227997, JP-A 06-041129, and JP-A 06-041130).

However, crystals of 2',3'-dideoxyinosine are decomposed during storage to produce hypoxanthine, and therefore it has been found that there is a problem in the long-term storage stability thereof.

SUMMARY OF THE INVENTION

Accordingly, it is one object of the present invention to provide novel methods for producing crystals of a purine nucleoside compound.

It is another object of the present invention to provide novel methods for producing crystals of 2',3'-dideoxyinosine.

It is another object of the present invention to provide novel methods for producing crystals of 2',3'-dideoxyinosine, which have excellent storage stability and resist decomposition during storage.

It is another object to provide novel crystals prepared by such a process.

These and other objects, which will become apparent during the following detailed description, have been achieved by the inventors' discovery that excellent storage stability can be obtained by regulating the concentration of phosphate attached to crystals of a purine nucleoside compound within a specific range. The present invention has been completed based on this finding.

Thus, the present invention provides:

(1) a method for producing crystals of a purine nucleoside compound which have a concentration of phosphate attached to the crystals of 25 ppm or more and have excellent storage stability,
said method comprising:
(i) preparing an aqueous solution comprising phosphate ion ($PO_4^{3-}$) and a purine nucleoside compound; and
(ii) crystallizing the purine nucleoside compound from the aqueous solution.

(2) A crystal of a purine nucleoside compound which has a concentration of phosphate attached to the crystal of 25 ppm or more and has excellent storage stability, which is prepared by a method comprising:
(i) preparing an aqueous solution comprising a phosphate ion ($PO_4^{3-}$) and a purine nucleoside compound; and
(ii) crystallizing the purine nucleoside compound from the aqueous solution.

DETAILED DESCRIPTION OF THE PREFERRED EMBODIMENTS

The method for producing crystals of a purine nucleoside compound of the present invention comprises preparing an aqueous solution comprising a phosphate ion ($PO_4^{3-}$) and a purine nucleoside compound.

Examples of the purine nucleoside compound which may be crystallized by the production method of the present invention include inosine, guanosine, adenosine, and 2',3'-dideoxy forms thereof. Among them, 2',3'-dideoxypurine nucleoside compounds such as 2',3'-dideoxy forms of inosine, guanosine, and adenosine are useful in the production method of the present invention. Particularly, 2',3'-dideoxyinosine is useful in the production method of the present invention.

Crystals of a purine nucleoside compound obtained by the production method of the present invention preferably have a concentration of phosphate attached to the crystals of 25 ppm or more, for example, 25 ppm to 2000 ppm. It is possible to improve the storage stability of crystals of a purine nucleoside compound by regulating the concentration of the phosphate within such a range. The concentration of the phosphate is more preferably 50 ppm or more, for example, 50 ppm to 2000 ppm.

The concentration of phosphate ion in an aqueous solution comprising a purine nucleoside compound is preferably 3 g/L or more, for example, 3 g to 20 g/L. It becomes easier to regulate the concentration of the phosphate attached to the finally obtained crystals of a purine nucleoside compound within an appropriate range by regulating the concentration of phosphate ion within such a range. The concentration of phosphate ion is more preferably 5 g/L or more, for example, 5 g to 20 g/L.

The phosphate ions in the solution may be added by adding a salt which contains phosphate anion. Suitable salts include, for example, sodium phosphate, potassium phosphate, etc.

Next, the method for producing the crystals of the purine nucleoside compound of the present invention comprises crystallizing out the purine nucleoside compound from the aqueous solution.

The crystallization methods of the purine nucleoside compound are not particularly limited, and the purine nucleoside compound can be crystallized by using a generally known crystallization devices and methods. The crystallization of the purine nucleoside compound may be conducted as described in U.S. Pat. No. 5,451,671, which is incorporated by reference herein in its entirety.

Further, the method for producing the crystals of the purine nucleoside compound of the present invention may comprise washing the obtained crystals of a purine nucleoside compound with water or an aqueous solution comprising a phosphate ion.

Washing of the crystals of the purine nucleoside compound with water or an aqueous solution comprising a phosphate ion is conducted so that the concentration of the phosphate attached to the crystals of the purine nucleoside compound is 25 ppm or more, for example, 25 ppm to 2000 ppm, and more preferably 50 ppm or more, for example, 50 ppm to 2000 ppm. The concentration of the phosphate ion of the aqueous solution comprising the phosphate ion for washing the crystals of a purine nucleoside compound is preferably 3 g/L or more, for example, 3 g/L to 20 g/L. It becomes easier to regulate the concentration of the phosphate attached to the finally obtained crystals of the purine nucleoside compound within an appropriate range by regulating the concentration of a phosphate ion within such a range. The concentration of the phosphate ion is more preferably 5 g/L or more, for example, 5 g/L to 20 g/L.

The concentration of the phosphate attached to the crystals of the purine nucleoside compound can be measured by the method comprising the steps of dissolving the crystals with water, and measuring the concentration thereof by column chromatography as described in this specification. The weight ratio of the measured phosphate to the crystals of the purine nucleoside compound is regarded as the concentration of the phosphate attached to the crystals.

Other features of the invention will become apparent in the course of the following descriptions of exemplary embodiments which are given for illustration of the invention and are not intended to be limiting thereof.

EXAMPLES

Examples 1 to 4 and Comparative Examples 1 to 4

2',3'-dideoxyinosine was dissolved in an aqueous solution comprising 10 g/L of phosphate ion ($PO_4^{3-}$) to obtain an aqueous solution comprising 100 g/L of 2',3'-dideoxyinosine. Then, crystals of 2',3'-dideoxyinosine were isolated by concentration crystallization, and the thus-obtained crystals were washed with water. The following Table 1 shows the concentration of the phosphate attached to the surface of the obtained crystals of 2',3'-dideoxyinosine.

In order to examine the storage stability, the obtained crystals were stored at 60° C., at RH75% for 7 days. The following Table 1 also shows an increase of hypoxanthine in the crystals of 2',3'-dideoxyinosine after storage. For comparison, Table 1 also shows data on crystals of 2',3'-dideoxyinosine which were produced by the same method as the above one except that 2',3'-dideoxyinosine was dissolved in an aqueous solution which did not comprise phosphate ion ($PO_4^{3-}$).

TABLE 1

|  | Phosphate radical conc. on the surface of crystals (ppm/DDI) | Increase of hypoxanthine after storage (%/DDI) |
|---|---|---|
| Ex. 1 | 480 | 0.45 |
| Ex. 2 | 90 | 0.48 |
| Ex. 3 | 150 | 0.20 |
| Ex. 4 | 140 | 0.54 |
| Comp. Ex. 1 | 0 | 2.24 |
| Comp. Ex. 2 | 0 | 1.91 |
| Comp. Ex. 3 | 0 | 2.21 |
| Comp. Ex. 4 | 0 | 2.20 |

From the above results, it is clarified that the increase of hypoxanthine of each of Examples 1 to 4 is less than that of each of Comparative Examples 1 to 4 which have the concentration of the phosphate on the surface of the crystals of 0 ppm.

The concentration of the phosphate on the surface of the crystals and the amount of hypoxanthine were analyzed in the conditions shown in the following Table 2.

TABLE 2

|  | Phosphate radical conc. | Hypoxanthine amount |
|---|---|---|
| Device | DIONEX ICS-1500 | HPLC |
| Column | Ionopak AS12A 4 × 200 mm | Shiseido CAPCELLPAK C18 4.6 × 250 mm |
| Column temp. | 35° C. | 40° C. |
| Suppressor | ASRS-ULTRA II-4 mm | — |
| Suppressor current v. | 60 mA | — |
| Analysis time | 15 min. | 15 min. |
| Eluent/mobile phase | 2.7 mM $Na_2CO_3$, 0.3 mM $NaHCO_3$ | Distilled water:acetonitile (92.5:7.5) |
| Eluent/mobile ph. flow | 1.5 ml/min. | 1.2 ml/min. |
| Detector | Conductance meter | Absorptionmeter |

Comparative Example 5

The crystals of 2',3'-dideoxyinosine of Example 3 were further suspended in water to remove the phosphate attached to the surface thereof. Using the obtained crystals of 2',3'-dideoxyinosine, the storage stability thereof was examined by the same method as that of Example 1. The following Table 3 shows results thereof together with those of Example 3.

TABLE 3

|  | Phosphate radical conc. on the surface of crystals (ppm/DDI) | Increase of hypoxanthine after storage (%/DDI) |
|---|---|---|
| Ex. 3 | 150 | 0.20 |
| Comp. Ex. 5 | 0 | 4.32 |

From the above results it is clarified that though crystals of 2',3'-dideoxyinosine were crystallized from an aqueous solution comprising a phosphate ion, when the phosphate attached to the surface of the crystals were removed by washing them with water, the hypoxanthine amount thereof increases.

Examples 5 to 13 and Comparative Examples 6 to 10

2',3'-dideoxyinosine was dissolved in an aqueous solution comprising 10 g/L of phosphate ion ($PO_4^{3-}$) to obtain an aqueous solution comprising 100 g/L of 2',3'-dideoxyinosine. Then, crystals of 2',3'-dideoxyinosine were isolated by concentration crystallization, and the thus-obtained crystals were washed with water. At that time, the degree of washing was changed per each sample, and the samples having the concentration of the phosphate attached to the crystals of 2',3'-dideoxyinosine as shown in the following Table 4 were obtained. Using the obtained crystals of 2',3'-dideoxyinosine, the storage stability were examined by the same method as that of Example 1. The following Table 4 shows results thereof.

TABLE 4

| | Phosphate radical conc. on the surface of crystals (ppm/DDI) | Increase of hypoxanthine after storage (%/DDI) |
|---|---|---|
| Comp. Ex. 6 | 0 | 2.47 |
| Comp. Ex. 7 | 0 | 2.24 |
| Comp. Ex. 8 | 0 | 2.20 |
| Comp. Ex. 9 | 6 | 2.21 |
| Comp. Ex. 10 | 8 | 1.91 |
| Ex. 5 | 26 | 1.38 |
| Ex. 6 | 29 | 1.03 |
| Ex. 7 | 41 | 1.19 |
| Ex. 8 | 45 | 0.90 |
| Ex. 9 | 52 | 0.70 |
| Ex. 10 | 76 | 0.97 |
| Ex. 11 | 118 | 0.90 |
| Ex. 12 | 138 | 1.26 |
| Ex. 13 | 173 | 1.04 |

From the above results, it is clarified that the increase of hypoxanthine of each of Comparative Examples 6 to 10 having the concentration of the phosphate on the surface of the crystals of less than 25 ppm is more than that of each of Examples 5 to 13 having the concentration of the phosphate on the surface of the crystals of 25 ppm or more.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for producing crystals of a purine nucleoside compound which have a concentration of phosphate attached to the crystals of 25 ppm or more,
said method comprising:
    (i) preparing an aqueous solution comprising phosphate ion ($PO_4^{3-}$) and a purine nucleoside compound; and
    (ii) crystallizing said purine nucleoside compound from said aqueous solution, to obtain crystallized purine nucleoside compound.

2. The method for producing crystals of a purine nucleoside compound according to claim 1, which further comprises:
    (iii) washing said crystallized purine nucleoside compound with water or an aqueous solution comprising a phosphate ion.

3. The method for producing crystals of a purine nucleoside compound according to claim 1, wherein said purine nucleoside compound is a 2',3'-dideoxypurine nucleoside compound.

4. The method for producing crystals of a purine nucleoside compound according to claim 2, wherein said purine nucleoside compound is a 2',3'-dideoxypurine nucleoside compound.

5. The method for producing crystals of a purine nucleoside compound according to claim 3, wherein said 2',3'-dideoxypurine nucleoside compound is 2',3'-dideoxyinosine.

6. The method for producing crystals of a purine nucleoside compound according to claim 4, wherein said 2',3'-dideoxypurine nucleoside compound is 2',3'-dideoxyinosine.

7. The method for producing crystals of a purine nucleoside compound according to claim 1, wherein the concentration of the phosphate attached to the surface of the purine nucleoside compound is 50 ppm or more.

8. The method for producing crystals of a purine nucleoside compound according to claim 2, wherein the concentration of the phosphate attached to the surface of the purine nucleoside compound is 50 ppm or more.

9. The method for producing crystals of a purine nucleoside compound according to claim 5, wherein the concentration of the phosphate attached to the surface of the purine nucleoside compound is 50 ppm or more.

10. The method for producing crystals of a purine nucleoside compound according to claim 6, wherein the concentration of the phosphate attached to the surface of the purine nucleoside compound is 50 ppm or more.

11. Crystals of a purine nucleoside compound which have a concentration of phosphate attached to the crystals of 25 ppm or more, which are prepared by a method comprising:
    (i) preparing an aqueous solution comprising phosphate ion ($PO_4^{3-}$) and a purine nucleoside compound; and
    (ii) crystallizing said purine nucleoside compound from said aqueous solution, to obtain crystallized purine nucleoside compound.

12. The crystals of a purine nucleoside compound according to claim 11, wherein said method further comprises:
    (iii) washing said crystallized purine nucleoside compound with water or an aqueous solution comprising a phosphate ion.

13. The crystals of a purine nucleoside compound according to claim 11, wherein said purine nucleoside compound is a 2',3'-dideoxypurine nucleoside compound.

14. The crystals of a purine nucleoside compound according to claim 12, wherein said purine nucleoside compound is a 2',3'-dideoxypurine nucleoside compound.

15. The crystals of a purine nucleoside compound according to claim 13, wherein said 2',3'-dideoxypurine nucleoside compound is 2',3'-dideoxyinosine.

16. The crystals of a purine nucleoside compound according to claim 14, wherein said 2',3'-dideoxypurine nucleoside compound is 2',3'-dideoxyinosine.

17. The crystals of a purine nucleoside compound according to claim 10, wherein the concentration of the phosphate attached to the surface of the purine nucleoside compound is 50 ppm or more.

18. The crystals of a purine nucleoside compound according to claim 12, wherein the concentration of the phosphate attached to the surface of the purine nucleoside compound is 50 ppm or more.

19. The crystals of a purine nucleoside compound according to claim 15, wherein the concentration of the phosphate attached to the surface of the purine nucleoside compound is 50 ppm or more.

20. The crystals of a purine nucleoside compound according to claim 16, wherein the concentration of the phosphate attached to the surface of the purine nucleoside compound is 50 ppm or more.

* * * * *